United States Patent [19]

Denk

[11] Patent Number: 5,728,856

[45] Date of Patent: Mar. 17, 1998

[54] SILYLENE, A PROCESS FOR ITS PRODUCTION AND ITS USE

[76] Inventor: Michael Denk, Lautererstrasse 14, D-81545 München, Germany

[21] Appl. No.: 553,320

[22] PCT Filed: May 16, 1994

[86] PCT No.: PCT/EP94/01578

§ 371 Date: Jan. 18, 1996

§ 102(e) Date: Jan. 18, 1996

[87] PCT Pub. No.: WO94/26752

PCT Pub. Date: Nov. 24, 1994

[30] Foreign Application Priority Data

May 19, 1993 [DE] Germany ............... 43 16 883.3

[51] Int. Cl.$^6$ ............... C07F 7/08; C07F 7/10
[52] U.S. Cl. ............... 556/407; 556/10; 546/6; 546/14
[58] Field of Search ............ 556/407, 10; 546/6, 546/14

[56] References Cited

U.S. PATENT DOCUMENTS 3,030,745 7/1962 Weber et al. ............... 556/407
3,509,194 4/1970 Fink ............... 556/407

FOREIGN PATENT DOCUMENTS 42 34 998 4/1994 Germany .

OTHER PUBLICATIONS

Article: Chemische Berichte, "Spektroskopischer Nachweis eines Bis(amino)silylens", vol. 125, Jun. 1992 (pp. 1375–1377).

Article: Chemische Berichte, "Decamethylsilicocene—The First Stable Silicon(II) Compound: Synthesis, Structure, and Bonding", P. Jutzi et al, vol. 122, 1989 (pp. 1629–1639).

Article: Journal of the American Chemical Society, "A Stable Crystalline Carbene", A. J. Arduengo, III et al, vol. 113, Jan. 1991 (pp. 361–362).

Article: Chemische Berichte "[2+2]–Cycloadditionen: Synthese von 1,4–Diaminnno–1,3–butadiiiien–2,3–dicarbonsäure–Derivaten", T. Dieck et al, vol. 102, 1987 (pp. 795–801).

Article: Journal of the American Chemical Society "Synthesis and Structure of a Stable Silylene", M. Denk et al, vol. 116, No. 6, Mar. 23, 1994, (pp. 2691–2692).

Article: Journal of the Chemical Society, Chemical Communications "Silylene Complexes from a Stable Silylene . . . Donor–free Bis–silylene Complex", No. 1, Jan. 7, 1994 (pp. 33–34).

Article: Taschenlehrbuch Der Organischen Chemie, Part A: Theoretische Und Allgemeine Gebiete, "Reaktive Zwischenstufen I", Georg Thieme–Verlag Stuttgart, C. Wentrup, vol. 8, 1979 (p. 203).

Article: Journal of the American Chemical Society, No. 53, Aug. 1931 (p. 3045).

Article: Chemikon, 1972 (V/43).

*Primary Examiner*—Paul F. Shaver
*Attorney, Agent, or Firm*—Burns, Doane, Swecker & Mathis, LLP

[57] ABSTRACT

Stable silylenes, and analog carbenes are prepared.

35 Claims, No Drawings

SILYLENE, A PROCESS FOR ITS PRODUCTION AND ITS USE

DESCRIPTION

The invention relates to stable silylenes, processes for producing such silylenes and analog carbenes as well as selected uses of the silylenes in accordance with the invention.

Silylenes, like carbenes, are very reactive owing to the problematic stabilization of divalent silicon compounds with free electron pair and have therefore been very difficult to isolate in substance until now.

In 1992 Veith et al. ("Chemische Berichte" [Chemical Reports] Volume 125, June 1992, p. 1375–1377) postulated for the first time a silylene as a result of a compound intercepted IR-spectroscopically at temperatures below 77 K. They formulated the silylene, because it could have originated intermediary during a photolysis reaction. A specific allocation of the spectrum in question with the formula "2d" of a silylene as given in the article is not made. The given publication also lacks a production approach for synthesizing the postulated silylene.

Silylenes are highly desired structural elements in the chemical synthesis owing to their reactivity.

It is thus the object of the present invention to provide stabilized, and therefore isolatable silylenes and a process for their production which can also be applied for analog carbon compounds.

This invention achieves this object by the materials as given in the independent claim 1 and by the process as given in the independent claim 7. Uses of the materials in accordance with the invention are obtained from the independent claims 36 to 40. Further advantageous embodiments of the materials and the process in accordance with the invention can be obtained from the dependent claims, the description and the examples.

The invention is based on the general recognition that silylenes can be stabilized by adjacent amido groups and furthermore that divalent silicon and carbon compounds can be prepared from the respective dihalogeno compounds by reduction with metals. The subject matter of the invention is therefore a silylene of the general formula I

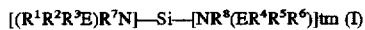

in which $R^1, R^2, R^3, R^4, R^5, R^6, R^7$ and $R^8$ are the same or different and each mean a hydrogen or halogen atom or an alkyl, aryl, alkoxy, aryloxy, amido or heteroaryl residue, and $R^7$ and $R^8$ can also represent the residue $-ER^1R^2R^3$ or $-ER^4R^5R^6$, and E means an element of the fourth main group of the periodic system of elements with the exception of lead and $R^7$ and $R^8$ can jointly form with the respective adjacent nitrogen atoms and the central silicon atom an optionally unsaturated heterocyclic ring with at least 4 ring atoms and furthermore a process for producing compounds of the general formula IV

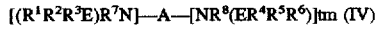

in which A means a silicon or carbon atom and $R^1, R^2, R^3, R^4, R^5, R^6, R^7, R^8$ and E have the aforementioned meanings, characterized in that a compound with the general formula (V)

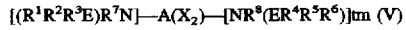

in which $A, R^1, R^2, R^3, R^4, R^5, R^6, R^7, R^8$ and E have the aforementioned meanings and X represents a hydrogen or halogen atom, optionally in the presence of a solvent, is converted with a reducing agent.

It has proved to be particularly advantageous in stabilizing the silylene in accordance with the invention to insert the two amido nitrogen atoms into a ring skeleton, preferably a hydrocarbon ring skeleton. In this respect the ring to be formed can consist of at least 4, preferably 4 to 10, particularly 4 to 6, ring atoms. Of particular advantage is the formation of an aromatic under inclusion of the respective free electron pairs on the nitrogen into the 6 ($\pi$) electron system. Preferably, an olefinic double bond is sufficient as a bridge-type cross-link between the amido nitrogen atoms. In a five-membered ring thus obtained two hydrogen atoms are preferably located at the olefinic double bond as ring substituent. The formed aromatic heterocycle can preferably also be stabilized by fused benzole or cyclopentadienyl nuclei. Other aromatic nuclei can also be fused. Various other, preferably bulky and electron-pushing groups such as alkyl, aryl, alkoxy, aryloxy, amido or heteroaryl groups can be situated at the nitrogen atom. Alkyl and aryl groups have proved to be advantageous. Particularly advantageous are alkyl or aryl groups with 1 to 20 C atoms, preferably with 1 to 10 C atoms and in particular such with 1 to 7 C atoms. The alkyl groups can be both straight-chained as well as branched, but preferably branched. Further preferred substituents at the nitrogen are the following: phenyl, mesityl, 2-pyridyl, 3-pyridyl, 4-pyridyl, dimethylamido and methoxy groups. This class of compounds is described in claims 1 and 2.

In another preferred embodiment of the silylenes in accordance with the invention the amido nitrogen atoms are inserted into a saturated heterocycle which preferably contains at least also one carbon atom, preferably 2 to 3 carbon atoms. It could also comprise no carbon atom, but any other element from the 4th main group of the periodic system of elements, with the exception of lead.

Additional favourable substituents in the silylenes in accordance with the invention are obtained from the selection of the classes of materials as given in claims 1 to 6.

In carrying out the process, the use of metals as reducing agents, in particular of alkali metals and their alloys, have proved to be advantageous for splitting off the halogen substituents of the starting materials. The alkali metals of lithium, sodium and/or potassium and alloys of these three metals among each other or with other electropositive elements whose melting point is below that of potassium are preferably used in the process in accordance with the invention.

The alloys of $Na_xK_y$ and $Li_xK_y$ have proved to be particularly favourable. x, y can be the same or different and can represent a value between 0.2 and 5, preferably between 0.5 and 3 and even more preferably between 1 and 2.5. An alloy of the approximate composition $Na_2K$ is used most preferably as reducing agent.

The reaction of potassium or a potassium alloy in an inert solvent with the starting materials as mentioned in claims 7, 31 and 32 has proved to be particularly advantageous. For the reduction it is necessary that the reaction temperature lies above the melting point of potassium (63.50° C.) or the potassium alloy. Advantageously, the reaction temperature should be in a range between room temperature and 200° C., preferably between 25° and 120° C. and particularly between 30° and 90° C.

It has further proved to be advantageous to use the reducing agent, e.g. the potassium alloy, in excess with respect to the starting material. At least 3 times the mole equivalent of potassium or potassium alloy and at least 2 times, preferably at least 2.2 times, of sodium, sodium alloy or any other reducing agent with respect to the starting material have proved to be particularly advantageous.

With the method in accordance with the invention it is possible to isolate stable silylenes and carbenes and to process them by means of distillation.

The filtration of the product after the conversion for separating solid residues, the draining of the solvent and the crystallization have proved to be satisfactory as further cleaning and isolating possibilities. The disposal of the hazardous, finely dispersed filtration residues occurs by way of covering with a layer of the same volume of inert solvent, e.g. a hydrocarbon such as pentan or hexan, and dropwise addition of an alcohol, e.g. i-propanol.

Furthermore, the formed silylene can also be used directly for a further step in the synthesis, i.e. without prior isolation and cleaning.

The materials mentioned in claims 7, 30, 31 and 32 are preferably suitable as starting materials. In formula V each residue X stands for a hydrogen atom or halogen atom. The remaining substituents are selected according to their property to stabilize the carbene or silylene to be formed.

Inert hydrocarbons, any saturated or aromatic ones, are preferably used as solvents. The use of hexan, particularly n-hexan, has proved to be advantageous in the conversion with potassium or a potassium alloy.

The process can be carried out at any pressure up to 101300 bar. Advantageously, the pressure should be in a range between 304 bar and 2533 bar, preferably between 709 bar and 1520 and particularly between 1013 bar and 1317 bar.

A preferred embodiment of the process under use of alkali metals or an alkali metal alloy as reducing agent is carried out under increased pressure. The selection of the solvent is not limited to such whose boiling point is above the melting point of the reducing agent.

In a further embodiment of the process sodium or lithium in elementary form or as main component of the alloy are used as reducing agent. The addition of a catalyst is advantageous for splitting off the halogen substituents from the starting materials.

Suitable catalysts are polynuclear aromatics such as anthracene, naphthalene, phenathrene, biphenyl, the mono- or poly-aza-derivatives of these compounds, in particular 2,2'-bipyridyl (=2,2'-diazabiphenyl), the alkyl derivatives of the aforementioned hydrocarbons and the derivatives thereof as well as the ethers and tertiary amines derived from said parent substances, which in addition to the aforementioned parent substances may also carry aromatic and/or aliphatic residues as substitutents.

Moreover, transition metal halogenides can be used as catalysts, preferably binary, their adducts with Lewis bases, in particular such with ethers, amines and phosphines, and their cyclopentadienyl derivatives, in particular of the general formula $CpMX_{m-1}$ or $Cp_2 MX_{m-2}$, in which M, X and m have the aforementioned meaning and Cp represents a cyclopentadienyl residue, and their adducts with Lewis bases.

The compounds of the general type $MX_m$ have proved to be advantageous, with M representing one of the following metals Ti, V, Nb, Ta, Cr, Mo, W, Mn, Re and $X_m$ any combination of the halogenides fluorine, chlorine, bromine and/or iodine and m can mean the numbers 2 to 4 in case of the metals Ti, V, Nb, Ta, Mo, W, Mn and Re and in the case of the metals Nb, Ta, Mo, W the number 5 and in the case of metal W also 6. Preferably, the binary halogen compounds of the elements Ti, V, Cr, Mo and W are used.

Moreover, catalysts such as crown ether and cryptands and derivatives of ethylene diamine which are completely substituted at the nitrogen atoms have proved to be advantageous for the reducing reaction pursuant to claim 19.

The catalyst is added in quantities of preferably approx. 1 mole % referred to the starting material.

When using sodium/lithium as reducing agent, any inert solvent can be used. Aryl and alkyl ether, however, have proved to be particularly advantageous, like the ones mentioned in claim 28.

The duration of the process is usually several days. Depending on the reactivity of the halogen catcher it may be up to 10 days or more in the process in accordance with the invention. When using potassium as reducing agent it is 2 to 4 days, and 2 to 7 days when using sodium/lithium as reducing agent.

The process supplies the products in yields between 50 and 95% of theory, referred to the starting materials used.

Further preferable embodiments of the materials and processes in accordance with the invention and possible uses are given in the subclaims.

Below, the process in accordance with the invention is described by reference to the examples 1 to 3 and a silylene in accordance with the invention is described by reference to selected material characteristics:

EXAMPLE 1

Reduction with potassium without catalyst:

53.59 g [N,N'-bis-(tert.-butyl)-1,4-diazabutene]-dichlorosilane (0.201 mole), dissolved in 600 ml n-hexan, is boiled in 3 mole equivalents potassium (23.52 g, 0.603 mole) in an argon atmosphere under return flow until an $^1$H-NMR-spectrum shows the absence of educt (1.21 ppm, 5.72 ppm). The cooled reaction mixture is filtered through a G3 fritted glass filter (with a diameter as large as possible, but not less than 4 cm) and the grey-blue contents of the frit (KCl+finely dispersed potassium) is washed with 2 portions of 100 ml pentan each. The removal of the solvent under vacuum and distillation through a solids distillation bridge (Kp=85°–86° C./33 mbar) supplies 22 to 30 g (57–78% of theory) [N,N'-bis-(tert.-butyl)-1,4-diazabutene]-silylene in form of colourless crystal needles.

EXAMPLE 2

Reduction with sodium and naphthalene as catalyst:

53.59 g [N,N'-bis-(tert.-butyl)-1,4-diazabutene]-dichlorosilane (0.201 mole) and 250 mg naphthalene, dissolved in 350 ml THF, is mixed three days in an argon atmosphere with 2.2 mole equivalents of sodium (10.17 g, 0.603 mole). After the addition of 300 ml pentan, filtering is carried out through a G3 fritted glass filter with a diameter as large as possible, but not less than 4 cm) and the grey-blue contents of the frit (NaCl+sodium) is washed with 2 portions of 100 ml pentan each. The product (31 to 35 g, 79–90% of theory) can be used without distillation.

EXAMPLE 3

Reduction with sodium and titanium trichloride as catalyst:

53.59 g [N,N'-bis-(tert.-butyl)-1,4-diazabutene]-dichlorosilane (0.201 mole) and 250 mg $TiCl_3$ or $TiCl_3$ $(THF)_3$naphthalene, dissolved in 350 ml THF, are mixed three days in an argon atmosphere with 2.2 mole equivalents of sodium (10.17 g, 0.603 mole). After the addition of 300 ml pentan, filtering is carried out through a G3 fritted glass filter (with a diameter as large as possible, but not less than 4 cm) and the grey-blue contents of the frit (NaCl+sodium) is washed with 2 portions of 100 ml pentan each. The product (27 to 30 g, 69–77% of theory) can be used without distillation.

The product of [N,N'-bis-(tert.-butyl)-1,4-diazabutene]-silylene produced in the examples 1 to 3 is a silylene in accordance with the invention and is to be described by reference to selected material characteristics.

The compound has the following empirical formula C$_{10}$H$_{20}$N$_2$Si and thus a molecular weight of 196.

Moreover the compound is represented by the following structural formula:

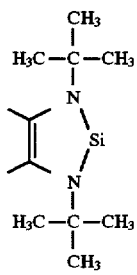

The compound is solid at room temperature (melting point 85° C.). It is colourless, air and water sensitive, but thermostable until at least 200° C. The compound crystallizes in form of crystal needles.

The isolation and cleaning is possible by distillation of the compound at 33 mbar and 85° to 86° C.

Characteristic spectroscopic data are obtained from the NMR spectrum in C$_6$D$_6$ with the following chemical shifts:
δ$^1$H:

1.40 (s, t-Bu)

6.74 (s, CH=CH)

δ$^{13}$C:

30.3 (q, $^1$J=125.7 Hz, t-Bu)

54.0 (s, t-Bu)

120.0 (dd $^1$J=176.1 Hz, $^2$J=11.0 Hz)

δ$^{15}$N:

−162.5 (vs MeNO$_2$)

δ$_{29}$Si:

+78.4 (s)

In the mass spectrometer a molecular peak appears at 196 (molecular weight of the compound C$_{10}$H$_{20}$N$_2$Si=196). Further data from the mass-spectroscopic examination of the substance are the following:

EI—MS (40 eV):

196 (59) [M$^+$•]

181 (23)

140 (18)

125 (42)

99 (6)

84 (100)

57 (78)

The silylenes in accordance with the invention enlarges the organic synthesis by an important component, namely the isolatable silylenes which can therefore be employed in a purposeful way.

The silylenes in accordance with the invention react with all previously examined (π)-systems such as azobenzole, 1,3-dienes, ketones, azides and metal carbonyles.

Furthermore, the silylenes in accordance with the invention insert in SiSi-bonds and are therefore suitable not only for forming polysilanes with defined chain length, but also for modifying polysilanes.

Preferred uses of the material in accordance with the invention are, among others, the production of polysilanes of defined chain length, the insertion in SiSi-bonds, the modification of homogeneous or heterogeneous catalysts. Moreover, the materials in accordance with the invention can be used as reactive partners in gas separation processes and for the synthesis of compounds containing silyl groups.

I claim:

1. Silylenes of the general formula I

(I)

in which R$^1$,R$^2$,R$^3$,R$^4$,R$^5$,R$^6$,R$^7$ and R$^8$ are the same or different and each mean a hydrogen or halogen atom or an alkyl, aryl, alkoxy, aryloxy, amido or heteroaryl residue, and R$^7$ and R$^8$ can also represent the residue —ER$^1$R$^2$R$^3$ or ⁻ER$^4$R$^5$R$^6$, and E means an element of the fourth main group of the periodic system of elements with the exception of lead, and R$^7$ and R$^8$ can jointly form with the mutually adjacent nitrogen atoms and the central silicon atom a heterocyclic ring with 4 ring atoms or an optionally unsaturated heterocyclic ring with at least 5 ring atoms.

2. A silylene of the general formula II

(II)

in which R$^1$,R$^2$,R$^3$,R$^4$,R$^5$,R$^6$ and E have the meaning as given in claim 1 and R$^9$ and R$^{10}$ are each the same or different and each mean a hydrogen or halogen atom or an alkyl, aryl, alkoxy, aryloxy, amido or heteroaryl residue.

3. A silylene of the general formula III

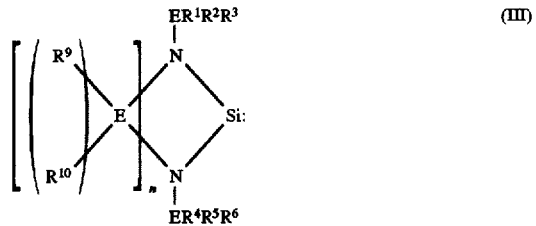

(III)

in which R$^1$,R$^2$,R$^3$,R$^4$,R$^5$,R$^6$,R$^9$,R$^{10}$ and E have the meaning as given in claim 1 or 2 and n is an integral number between 1 and 10.

4. The silylene as claimed in claim 1 or 2, characterized in that at least one of the residues R$^1$,R$^2$,R$^3$,R$^4$,R$^5$ and R$^6$ is a CH$_3$-group.

5. The silylene as claimed in claim 1 or 2, characterized in that at least one of the residues R$^9$ and R$^{10}$ is a hydrogen atom.

6. The silylene as claimed in claim 1 or 2, characterized in that n=2, 3 or 4.

7. A process for producing compounds of the general formula IV

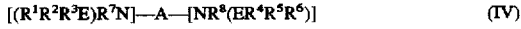

(IV)

in which A is a silicon or carbon atom and R$^1$,R$^2$,R$^3$,R$^4$,R$^5$, R$^6$,R$^7$,R$^8$ and E have the meanings as given in claim 1, characterized in that a compound of the general formula (V)

(V)

in which A,R$^1$,R$^2$,R$^3$,R$^4$,R$^5$,R$^6$,R$^7$,R$^8$ and E have the aforementioned meanings and X represents a hydrogen or halogen atom, optionally in the presence of a solvent, is converted with a reducing agent.

8. The process as claimed in claim 7, characterized in that an alkali metal or an alkali metal alloy is used as reducing agent.

9. The process as claimed in claim 8, characterized in that the reduction with the alkali metal or the alkali metal alloy is carried out in a solvent at a temperature above the melting point of the alkali metal or the alkali metal alloy.

10. The process as claimed in claim 8 or 9, characterized in that the alkali metal is potassium and that it is used in excess with respect to the starting material of the general formula (V).

11. The process as claimed in claim 7, characterized in that the formed silylene or carbene is isolated subsequently from the reaction mixture.

12. The process as claimed in claim 11, characterized in that the formed silylene or carbene is simultaneously cleaned during the isolation.

13. The process as claimed in claim 11, characterized in that the isolation of the silylene or carbene occurs by distillation.

14. The process as claimed in claim 11, characterized in that the isolation of the silylene or carbene occurs by crystallization.

15. The process as claimed in claim 7, characterized in that the process is carried out under an inert gas atmosphere.

16. The process as claimed in claim 7, characterized in that a hydrocarbon is used as solvent.

17. The process as claimed in claim 7, characterized in that it is carried out under increased pressure.

18. The process as claimed in claim 7, characterized in that it is carried out under reduced pressure.

19. The process as claimed in claim 7, characterized in that a catalyst is used.

20. The process as claimed in claim 19, characterized in that a solvent and, as a reducing agent, an alkali metal or alkali metal alloy are used.

21. The process as claimed in claim 19, characterized in that a compound is used as catalyst which comprises at least two aromatic rings.

22. The process as claimed in claim 21, characterized in that anthracene, naphthalene, phenathrene, biphenyl, an alkyl derivative, a mono- or poly-aza-derivative of these hydrocarbons, in particular 2,2'-bipyridyl or an ether derived from the parent substances of these compounds or a tertiary amine derived from the parent substances of these compounds are used as catalyst.

23. The process as claimed in claim 19, characterized in that a transitional metal halogenide of the formula $MX_m$ is used as catalyst, with the following meanings:

M=Ti, V, Nb, Ta, Cr, Mo, W, Mn or Re,

X=F, Cl, Br or J and m is an integral number of 2 to 4 for M=Ti, V, Nb, Ta, Mo, W, Mn, Re or the number 5 for M=Nb, Ta, Mo, W or the number 6 for M=W.

24. The process as claimed in claim 23, characterized in that a catalyst is added which is an adduct of a transitional metal halogenide with Lewis bases or a cyclopentadienyl derivative of a transitional metal halogenide, in particular of the general formula $CpMX_{m-1}$ or $Cp_2MX_{m-2}$, in which M, X and m have the meaning as given in claim 22 and Cp represents the cyclopentadienyl group.

25. The process as claimed in claim 24, characterized in that a catalyst is used in which M=Ti, V, Cr, Mo or W.

26. The process as claimed in one of the claims 24 or 25, characterized in that a catalyst is used in which X means a chlorine atom.

27. The process as claimed in claim 7, characterized in that an ether of the general formula $R^{11}$—O—$R^{12}$ is used as solvent in which the $R^{11}$ and $R^{12}$ are the same or different and are each an alkyl or aryl group.

28. The process as claimed in claim 27, characterized in that diethyl ether, tetrahydrofuran, 1,4-dioxan, 1,2-dimethoxyethane, 1-methoxy-2-ethoxyethane, diisopropyl ether, dibutyl ether, diglyme, triglyme or a crown ether are used as ether.

29. The process for producing the compounds of formula IV as claimed in claim 19, characterized in that the catalyst is added with a quantity of approx. 1 mole % referred to the starting material of the general formula V.

30. The process as claimed in claim 7, characterized in that a cyclic compound of the general formula V is used.

31. The process as claimed in claim 30, characterized in that a diamidohalogen silane (IV) of the general formula VI

is used as starting material, with $R^1,R^2,R^3,R^4,R^5,R^6$, $R^9,R^{10}$ and E having the meanings as given in claims 1 and 2 and X representing a hydrogen atom or a halogen atom.

32. The process for producing compounds of the general formula III

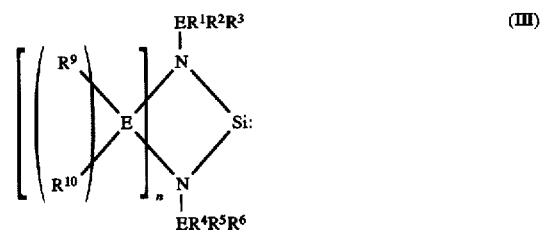

in which $R^1,R^2,R^3,R^4,R^5,R^6,R^9,R^{10}$ and E have the meaning as given in claim 1 or 2 and n is an integral number between 1 and 10, characterized in that a diamidohalogen silane (IV) of the general formula VII

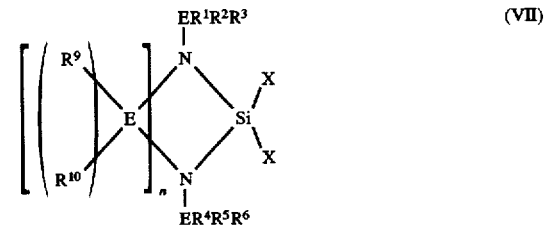

is used as starting material, in which $R^1,R^2,R^3,R^4,R^5,R^6,R^9$, $R^{10}$ and E have the meanings as given in claims 1, 2 and 7 and n represents the integral numbers as given in claim 3 and X means a hydrogen or a halogen atom.

33. The process as claimed in claim 31, characterized in that at least one of the residues $R^1,R^2,R^3,R^4,R^5$ and $R^6$ is a $CH_3$-group.

34. The process as claimed in claim 31, characterized in that at least one of the residues $R^9$ and $R^{10}$ is a hydrogen atom.

35. The process as claimed in claim 32, characterized in that n=2, 3 or 4.

* * * * *